(12) United States Patent
Wennerback (10) Patent No.: US 7,785,307 B2
(45) Date of Patent: Aug. 31, 2010

(54) PANT-TYPE ABSORBENT ARTICLE

(75) Inventor: Magareta Wennerback, Molnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 77 days.

(21) Appl. No.: 11/843,419

(22) Filed: Aug. 22, 2007

(65) Prior Publication Data
US 2007/0293833 A1 Dec. 20, 2007

Related U.S. Application Data

(63) Continuation of application No. PCT/SE2005/000307, filed on Mar. 2, 2005.

(51) Int. Cl.
*A61F 13/15* (2006.01)
*A61F 13/20* (2006.01)

(52) U.S. Cl. .............................. 604/385.01; 604/385.22

(58) Field of Classification Search ................ 604/358, 604/385.01, 385.22–385.3
See application file for complete search history.

(56) References Cited

U.S. PATENT DOCUMENTS

| | | | |
|---|---|---|---|
| 6,413,249 B1 * | 7/2002 | Turi et al. .................... | 604/387 |
| 6,476,289 B1 | 11/2002 | Buell et al. | |
| 6,552,245 B1 | 4/2003 | Roessler et al. | |
| 2002/0177829 A1 | 11/2002 | Fell et al. | |
| 2003/0088228 A1 * | 5/2003 | Desai et al. ............ | 604/385.24 |
| 2003/0217803 A1 | 11/2003 | Hermansson et al. | |
| 2004/0210205 A1 | 10/2004 | VanGompel et al. | |
| 2004/0243086 A1 | 12/2004 | VanGompel et al. | |

FOREIGN PATENT DOCUMENTS

| | | |
|---|---|---|
| EP | 1 035 818 | 4/2002 |
| EP | 1 473 008 A1 | 3/2004 |
| JP | 10-043235 | 2/1998 |
| JP | 2000-175966 A | 6/2000 |
| JP | 2003-290284 A | 10/2003 |

(Continued)

OTHER PUBLICATIONS

International Search Report Application No. PCT/SE 2005/000307 dated Dec. 15, 2007.

(Continued)

*Primary Examiner*—Michele Kidwell
(74) *Attorney, Agent, or Firm*—Buchanan Ingersoll & Rooney PC (57) ABSTRACT

A pant-type absorbent article having an absorbent assembly having an absorbent core and a chassis, wherein the front and back portions are joined to each other along two opposite longitudinal side edges to define a waist-opening and a pair of leg-openings, at least one of the front and back portions has an elastic web material, a crotch portion located between the front portion and the back portion in the longitudinal direction of the article, the front portion having a length in the longitudinal direction, the back portion having a length in the longitudinal direction, and the crotch portion having a length in the longitudinal direction, the absorbent assembly overlapping a distance with both the front and back portions, the article having a longitudinal and a transverse direction, wherein the absorbent assembly overlaps no more than 20% of the surface area of each of the front and back portions.

33 Claims, 4 Drawing Sheets

FOREIGN PATENT DOCUMENTS

| | | |
|---|---|---|
| WO | WO 96/11357 | 4/1996 |
| WO | WO 03/047488 | 6/2003 |
| WO | WO 2005/122985 | 12/2005 |
| WO | WO 2006/038837 | 4/2006 |

OTHER PUBLICATIONS

Notice of Reasons for Rejection dated Feb. 16, 2010 issued in corresponding Japanese Patent Application No. 2007-557955.

* cited by examiner

PANT-TYPE ABSORBENT ARTICLE

CROSS-REFERENCE TO RELATED APPLICATIONS

The present application is a continuation of PCT International Application No. PCT/SE2005/000307, filed on Mar. 2, 2005, and which designates the U.S. The entire contents of PCT/SE2005/000307 is incorporated herein by reference.

TECHNICAL FIELD

The present invention refers to a pant-type absorbent article such as a pant diaper, a sanitary pant or incontinence garment, said article comprising an elastic web material.

BACKGROUND

Absorbent articles having defined core regions and chassis regions are supposed to have a comfortable fit about the wearer. For pant articles like pant diapers, sanitary pants and incontinence pants it is also desirable that the articles are capable of being pulled up and down over the hips of the wearer to allow the wearer or caregiver to easily put on and remove the article when it has been soiled. It is known to make such absorbent pants with elasticized stretchable side portions and waist portion, usually comprising elastic members, such as elastic threads, contractably affixed between the backsheet and the topsheet.

It is further known to make portions of the chassis of absorbent articles of an elastic material, such as stretch-bonded laminates. Such laminates may include a layer of meltblown elastomeric fibers which have been stretched and sandwiched between outer layers of spunbonded webs.

U.S. Pat. No. 6,552,245 discloses an extensible outer cover for an absorbent article which provides a certain permanent deformation when subjected to a tensile force. The extensible outer cover comprises a necked laminate in the form of one layer of a necked non-elastic film and one layer of an elastic film. The films may be breathable.

WO 03/047488 discloses an elastic laminate comprising an elastic film which on opposite sides is bonded to first and second non-elastic fibrous layers. The laminate is made by bonding the non-elastic fibrous layers to the elastic film layer and subsequently stretching the composite material, causing the non-elastic materials to break. The elastic film material may be of a breathable material. The laminate may be incorporated in an absorbent article.

US 2004/0243086 discloses a disposable pant-like undergarment having stretchable front and back portions, for example made of an elastic laminate. An absorbent assembly is secured to the front and back portions.

Further examples of absorbent articles which in part are made of elastic laminates are found in U.S. Pat. No. 6,476,289 and JP 10043235.

International applications PCT/SE2004/001004, PCT/SE2004/001005 and PCT/SE2004/001415 refer to absorbent articles comprising an outer coversheet in the form of an elastic laminate having improved properties such as cloth-like feel and appearance.

To obtain good fit, improved comfort and security against leakage, it is important that absorbent articles have dimensions which match the relative dimensions of the wearer. The relative dimensions of the article are also important, so that the components or regions of the article are not excessively large or small relative to each other. The overall dimensions of the article and relative dimensions of its components may also be adjusted so as to obtain an article with a more pant-like appearance. Elastic materials may be used to improve fit, but these are often expensive, so a need exists for articles which are elastic in those parts where elasticity is important, yet may comprise (cheaper) inelastic material in those parts where elasticity is less important. The correct choice of elastic and inelastic materials must be made for the different components or regions of the article, thus balancing the interests of economy and good fit of the article. Furthermore, the elastic properties of the elastic web materials used in the construction of the article must be preserved wherever possible.

There is still need for improvement of the properties of absorbent articles comprising an elastic web material, such as an elastic laminate, particularly their fit and appearance. The comfort and soft feel of absorbent articles of the above-mentioned type is also important. Furthermore, improvements in manufacturing methods allow manufacturing costs to be kept to a minimum, which is important for disposable articles, as they are discarded after a single use.

OBJECT AND SUMMARY

An object of the present disclosure is to provide a pant-type absorbent article which avoids the problems associated with known articles of this type. This is achieved by a pant-type absorbent article (such as a pant diaper, a sanitary pant or incontinence pant) said article having an absorbent assembly comprising an absorbent core, and a chassis. The chassis comprises a front portion and a back portion, which are joined to each other along two opposite longitudinal side edges to define a waist-opening and a pair of leg-openings. At least one of the front and back portions comprises an elastic web material. The article further comprises a crotch portion located between the front portion and the back portion in the longitudinal direction of the article. The front portion has a length (b1) in the longitudinal direction, the back portion has a length (b3) in the longitudinal direction, and the crotch portion has a length (b2) in the longitudinal direction. The absorbent assembly lies at least in said crotch portion and overlaps a certain distance with both the front and back portions, and the article has a longitudinal (y) and a transverse direction (x).

According to one embodiment of the disclosure, the absorbent assembly overlaps no more than 20%, preferably no more than 10%, of the surface area of each of the front and back portions, as measured in an extended state of the article. The term "extended state" will be described more fully below.

In this way, the pant-type absorbent article provides good fit, improved comfort and security against leakage, as the article adapts to the shape of the wearer's body more easily. Using a combination of portions in particular parts of the article allows specification of the components more easily, and selection of those which are most suitable in a given portion.

In another embodiment of the disclosure, the article has a front half defined by the edges of the article and a transverse centre line of the article, and a rear half defined by the edges of the article and a transverse centre line of the article. The surface area of the front half is between 80% and 90% of the surface area of the rear half, as measured in an extended state of the article.

In a further embodiment, the article has a maximum width (c) in the transverse direction and a maximum length (b) in the longitudinal direction. The ratio of the maximum width (c) to the maximum length (b) of the article is between 80% and 120%, preferably between 90% and 110%, as measured in an extended state of the article. Furthermore, the ratio of the length (b1) of the front portion to the width (c) of the article may be between 25% and 35%, preferably between 28 and 32%, as measured in an extended state of the article. The ratio of the length (b3) of the back portion to the width (c) of the article may be between 38% and 52%, as measured in an extended state of the article.

The length (b2) of the crotch portion is between 10-40%, preferably between 20-40%, most preferably between 25-35% of the entire length of the article (b) as measured in an extended state of the article.

In one embodiment both of the front and back portions comprise said elastic web material.

According to one aspect of the disclosure the crotch portion is substantially free from said elastic web material and that the length of the crotch portion is substantially equal to the distance between panels of the elastic web material in the front and back portion.

Preferably, the absorbent assembly comprises a liquid impervious backsheet layer, a liquid pervious topsheet layer and an absorbent core enclosed therebetween.

In one embodiment, the crotch portion comprises crotch panel material, which is preferably a substantially inelastic web material, and which underlies the absorbent assembly on the garment-facing side thereof. Preferably, the inelastic web material is a nonwoven material.

According to one embodiment, the elastic web material is a laminate composed of first and second layers of fibrous material and an elastic film layer located between said first and second fibrous layers. In a further embodiment, the elastic film layer is breathable.

In one aspect of the disclosure the elastic laminate has a Water Vapour Transmission Rate according to ASTM E96-00 Procedure D of at least 1500 $g/m^2$ 24 h, preferably at least 3000 $g/m^2$ 24 h.

According to one embodiment, said elastic laminate comprises first and second fibrous layers of spunbond material, each having a basis weight of between 10 and 35 $g/m^2$, preferably between 12 and 30 $g/m^2$, more preferably between 10 and 25 $g/m^2$, and a breathable elastic film layer having a basis weight between 20 and 80 $g/m^2$, preferably between 20 and 60 $g/m^2$, said laminate having a Water Vapour Transmission Rate according to ASTM E96-00 Procedure D of at least 1500 $g/m^2$ 24 h, preferably at least 3000 $g/m^2$ 24 h.

According to a further embodiment, said elastic web material has an elasticity in the transverse direction of the article of at least 30%, preferably at least 50%, more preferably at least 70%, when measured according to the elasticity test specified herein.

In one aspect of the disclosure the elastic web material has a basis weight of no more than 100 $g/m^2$, preferably no more than 90 $g/m^2$.

BRIEF DESCRIPTION OF DRAWINGS

Embodiments of the invention will be described in the following in greater detail by way of example and with reference to the accompanying drawings, in which.

DETAILED DESCRIPTION OF PREFERRED EMBODIMENTS

Absorbent Article

The term "absorbent article" refers to products that are placed against the skin of the wearer to absorb and contain body exudates, like urine, faeces and menstrual fluid. The invention mainly refers to disposable absorbent articles, which means articles that are not intended to be laundered or otherwise restored or reused as an absorbent article after use. The invention refers to "pant-type absorbent articles", having a core region and a chassis region surrounding the core region. Examples of such pant-type absorbent articles are pant diapers, sanitary pants and incontinence pants.

The drawings show an embodiment of a pant diaper 1 for an infant or an incontinent adult. Said pant diaper typically comprises an absorbent core 2 located in the absorbent assembly 3 of the article. The diaper further comprises a chassis 4. The chassis comprises a front portion 5, a back portion 6. The article may comprise an elastic waist band 17.

Figure 4:
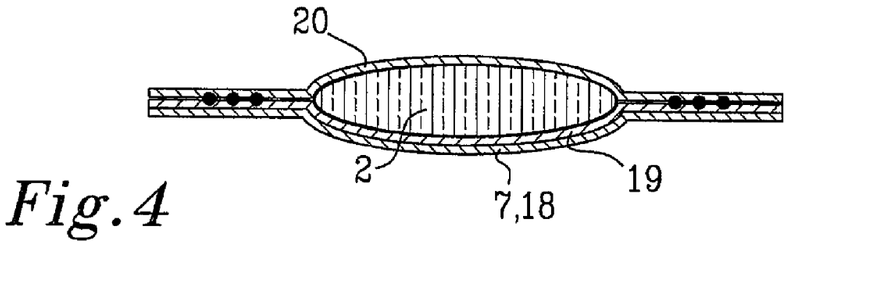
FIG. 4 is a cross section according to the line VI-VI in FIG. 3.

The article has a longitudinal direction y and a transverse direction x. The absorbent assembly 3 comprises a liquid pervious topsheet 20 and a liquid impervious backsheet 19. The absorbent core 2 is enclosed between the topsheet 20 and the backsheet 19 (FIG. 4).

Topsheet

The liquid pervious topsheet 20 can consist of a nonwoven material, e g spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and intended to be readily penetrated by body fluid, e.g. urine or menstrual fluid. The topsheet may be different in different parts of the absorbent article.

Backsheet

The liquid impervious backsheet 19 comprised in the absorbent assembly 3 on the garment-facing side of the absorbent core 2 is of a liquid impervious material, such as a thin plastic film, e.g. a polyethylene or polypropylene film, a nonwoven material coated with a liquid impervious material, a hydrophobic nonwoven material which resists liquid penetration or a laminate comprising plastic films and nonwoven materials. The backsheet 19 may be breathable so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens. The backsheet 9 is preferably inelastic.

Elastic Web Material

At least one of the front and back portions 5 and 6 of the chassis 4 comprises an elastic web material 10. Preferably both portions 5 and 6 comprise elastic web material 10. The elasticity in the x-direction of the elastic web material 10 should be at least 30%, preferably at least 50%, more preferably at least 70%, as measured by the elasticity test specified herein.

Preferably the elastic web material 10 is also elastic in the y-direction of the article. However the elasticity in the y-direction is preferably lower than in the x-direction. The elasticity in the y-direction should be at least 20%.

Figure 5:
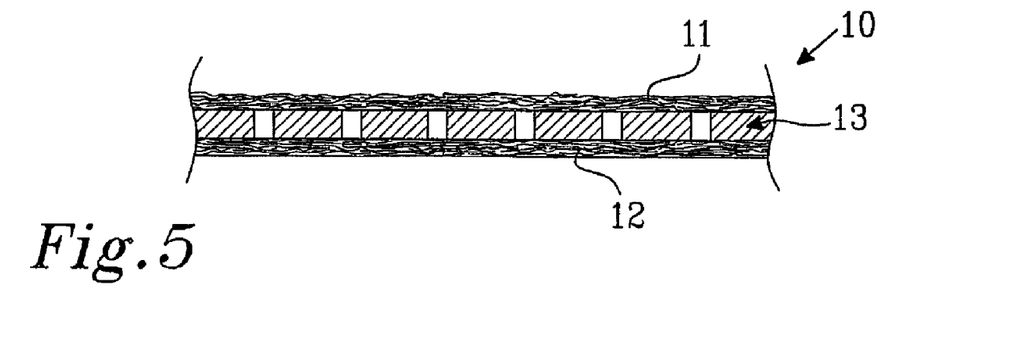
FIG. 5 is a cross section through an elastic laminate according to the line VII-VII in FIG. 3.

In the embodiment shown and described herein, the elastic web material is an elastic laminate 10 composed of first and second outer layers of fibrous material 11 and 12 and a middle elastic film layer 13 located between said fibrous layers (see FIG. 5). However it is understood that other types of elastic web materials may be used, such as elastic nonwoven materials, nonwoven materials which are per se inelastic, but which have been elastified by means of elastic threads etc. The elastic web materials may comprise one layer or two or more layers that have been laminated.

In the elastic laminate shown and described herein, it is preferred that the outer fibrous layers 11 and 12 are chosen so that they, in combination with the inner elastic film layer 13, give the material high resistance to puncture. They also provide a soft and cloth-like feel to the laminate. Examples of suitable materials are carded webs and spunbond materials. The basis weight of the fibrous material layers should be between 10 and 35 g/m$^2$, preferably between 12 and 30 g/m$^2$, more preferably between 15 and 25 g/m$^2$. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and through this, give the nonwoven material a higher elongation at maximum load. A mixture of polyethylene and polypropylene polymers has proved to provide good results in this respect. A mixture of fibers of different polymers is also possible.

The middle layer 13 is according to one embodiment of the invention an apertured elastic film having a basis weight between 20 and 80 g/m$^2$, preferably between 20 and 60 g/m$^2$. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

The total basis weight of the laminate is preferably 100 g/m$^2$ or less, more preferably no more than 90 g/m$^2$.

The elastic laminate 10 may be manufactured according to the method disclosed in WO 03/047488, wherein one spunbond layer 11 is applied to the film 13 in a tacky state and will thus bond to the film layer, while the other spunbond layer 12 is adhesively laminated to the film layer 13, using for example a pressure sensitive hot melt adhesive. Alternatively the laminate is manufactured according to a modified version of this known method, wherein the modification involves that the laminate is incrementally stretched (through intermeshing gears, IMG), to a point below the elongation at peak load of at least one of the non-elastic nonwoven layers to retain some strength for at least one of the nonwoven layers. The other layer may also be stretched to a point below its elongation at peak load, or to a point at which it will tear during stretching.

The method disclosed in WO 03/047488 involves stretching of the laminate above the point of failure of the fibrous material, so that the non-elastic layers break completely. Therefore, as described in WO 03/047488, the elongation of the laminate is not limited by the stretch modulus of the non-elastic material.

In a preferred embodiment at least one, preferably both fibrous layers, which are bound to the elastic film, are (in contrast to the method described in WO 03/047488) not completely torn upon manufacture of a laminate according to the present invention. Selection of fibrous materials which have an elongation at maximum load greater than the elasticity of the elastic laminate allows the elastic film to stretch without being hindered by the fibrous layers. Such a selection also ensures that the fibrous layers contribute to the puncture resistance of the laminate, as they are not completely torn or broken during manufacture. Preferably both fibrous layers or at least one of the fibrous layers have an elongation at maximum load that is at least 10% higher than the elasticity of the laminate. This is described in more detail in PCT/SE2004/001005, which is incorporated herein by reference.

The opacity of a material layer is the characteristic ability of the material layer to visually hide from view an underlying object or pattern. The opacity is measured in %, wherein 100% opacity means that nothing can be seen through the material layer and 0% means that the material layer is completely transparent. The opacity is measured by the Opacity Test described below, which is based on luminous-reflectance-factor data.

Opacity of the laminate can be obtained by the incorporation of opacifying fillers into the laminate, particularly into the elastic film. Such pigments can be organic or inorganic dyes, colouring agents, or whitening agents. Inorganic materials such as titanium dioxide, inorganic carbonates, synthetic carbonates, talc, nepheline syenite, magnesium hydroxide, aluminium trihydrate siatomaceous earth, mica, natural or synthetic silicas, calcinated clays and mixtures thereof are all examples of preferred opacifying fillers.

The filler is preferably added as a master batch at the extrusion of the film. One example of an appropriate concentration is about 5% filler by weight of the film.

It is further preferred that the elastic laminate 10 has a breathability (Water Vapour Transmission Rate) according to ASTM E96-00 Procedure D of at least 1500 g/m$^2$ 24 h, preferably at least 3000 g/m$^2$ 24 h.

The open area of the elastic film layer is preferably at least 5%, more preferably at least 8%. The open area is measured by image analysis methods and is defined as the sum of the hole area divided by the total area of the film sample.

Absorbent Core

The "absorbent core" is the absorbent structure disposed in the absorbent assembly of the absorbent article. The absorbent core 2 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times its weight and in an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like.

A high absorption capacity is provided by the use of high amounts of superabsorbent material. For an absorbent core comprising a matrix of hydrophilic fibers, such as cellulosic fibers, and superabsorbent material, the proportion of superabsorbent material is preferably between 10 and 90% by weight, more preferably between 30 and 70% by weight.

It is conventional in absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent polymers. The size and absorbent capacity of the absorbent core may be varied to be suited for different uses such as for infants or for adult incontinent persons.

The absorbent core may further include an acquisition distribution layer placed on top of the primary absorbent body and which is adapted to quickly receive and temporarily store discharged liquid before it is absorbed by the primary absorbent core. Such acquisition distribution layers are well known in the art and may be composed of porous fibrous waddings or foam materials.

Pant Diaper

Figure 1:
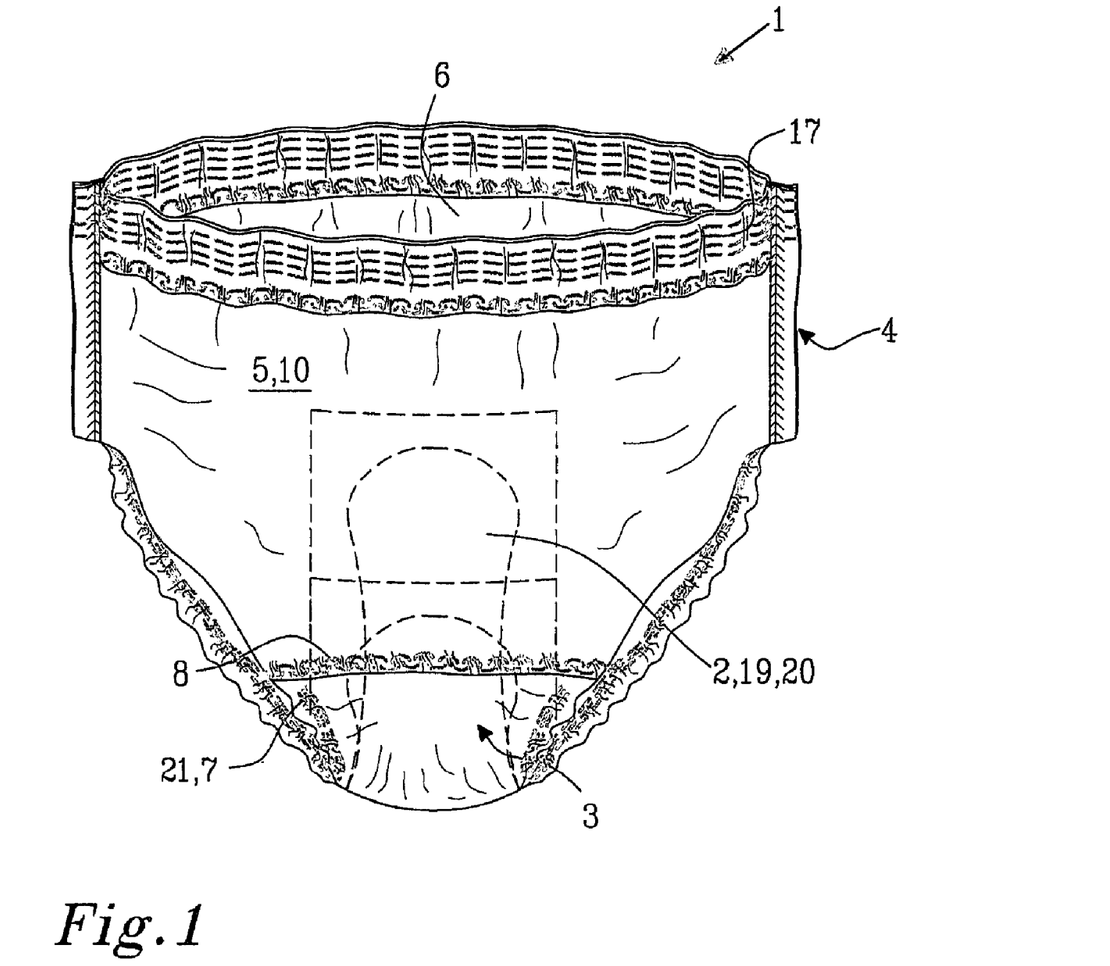
FIG. 1 shows a perspective view of a pant diaper according to an embodiment of the present invention.

The pant diaper disclosed in FIG. 1 is intended to enclose the lower part of the wearer's trunk like a pair of underwear. It comprises an absorbent assembly 3 and a chassis 4. The chassis 4 comprises a front portion 5 and a back portion 6. The front 5 and back portions 6 are joined to each other along two opposite longitudinal side edges by ultrasonic welds, glue strings or the like to define a waist-opening and a pair of leg-openings of the pant diaper.

At least one and preferably both of the front and back portions 5,6 comprises an elastic web material 10 as described above. The absorbent assembly 3 lies at least in said crotch portion 7 and overlaps a certain distance with both the front and back portions 5; 6, and the article has a longitudinal (y) and a transverse direction (x).

The article 4 further comprises a crotch portion 7 located between the front portion 5 and the back portion 6 in the longitudinal direction of the article. The front portion 5 has a length b1 in the longitudinal direction, the back portion 6 has a length b3 in the longitudinal direction, and the crotch portion 7 has a length b2 in the longitudinal direction.

Figure 2:
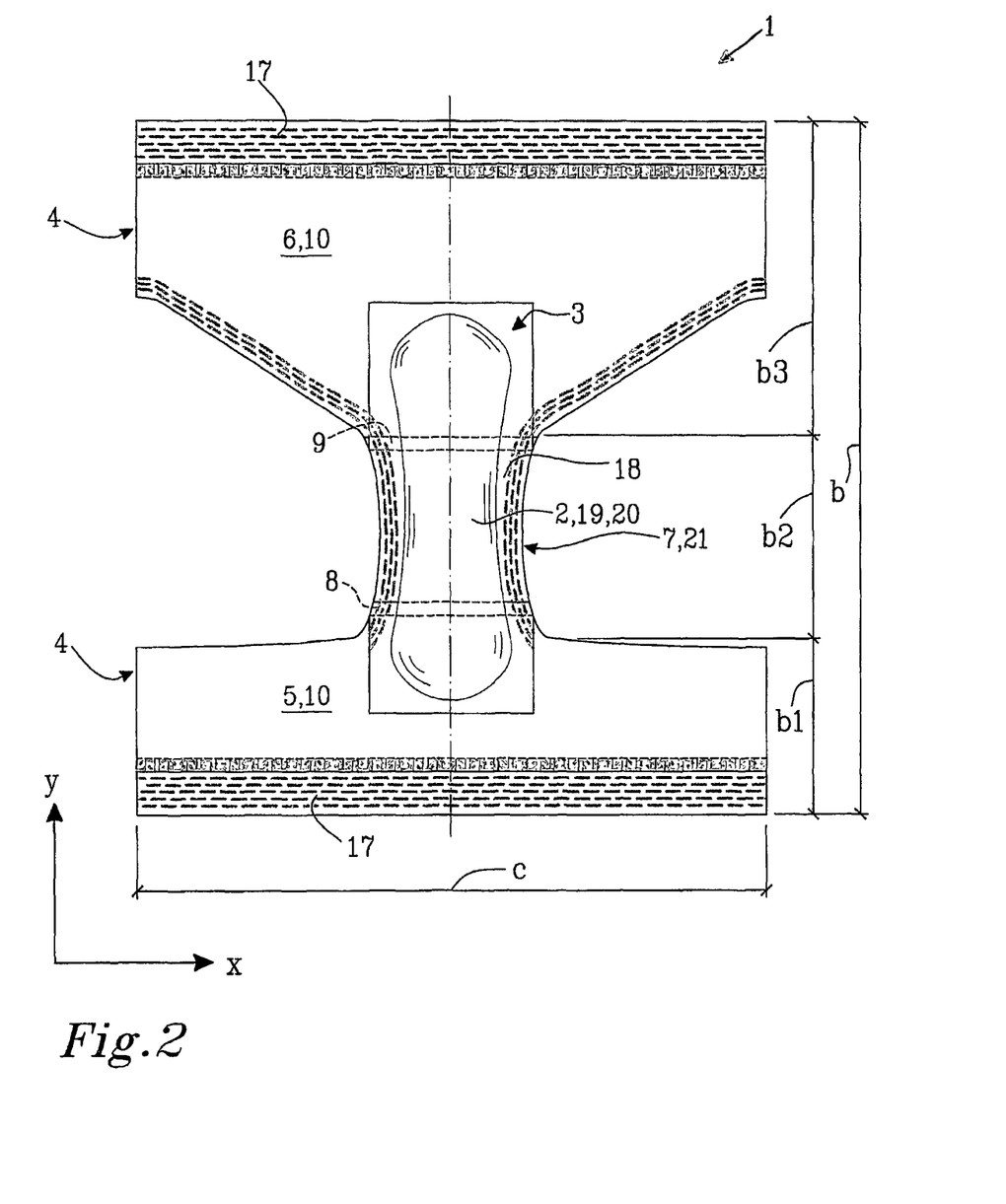
FIG. 2 shows is a plan view of the pant diaper in its flat, fully-extended state prior to formation as seen from the body-facing side.
Figure 3:
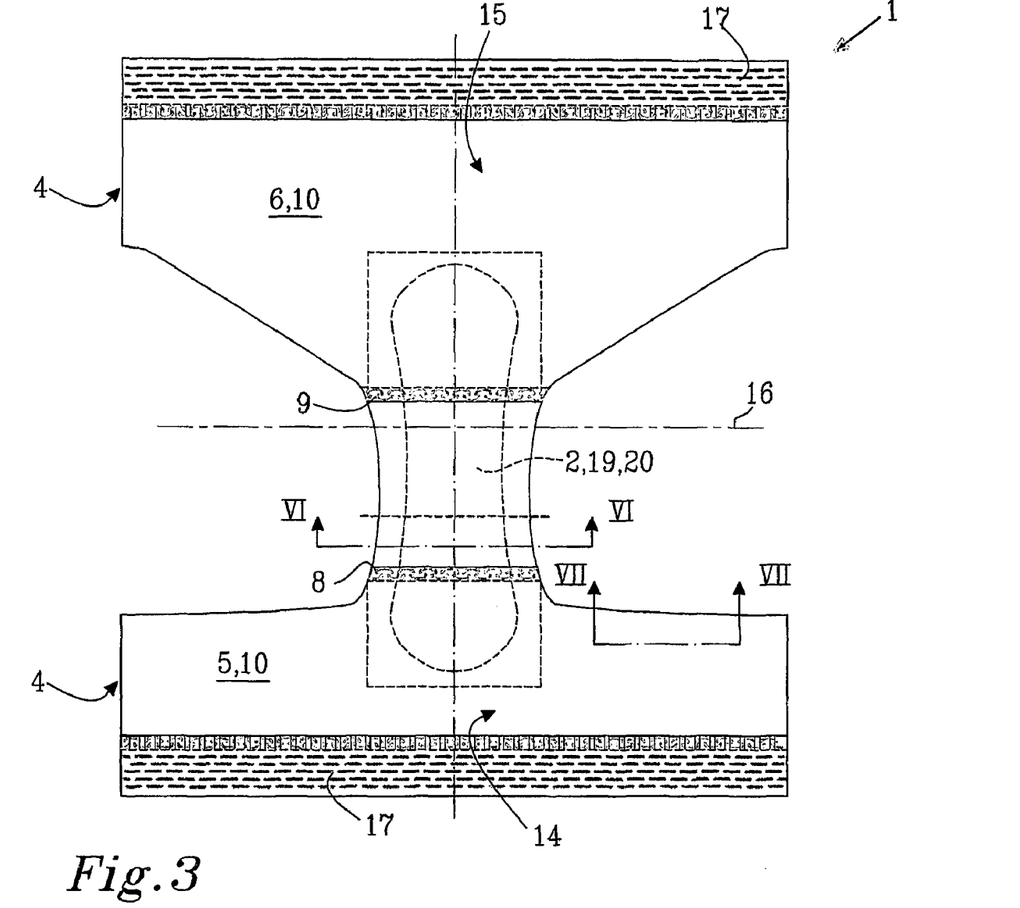
FIG. 3 is a corresponding plan view from the opposite, garment-facing side of the pant diaper.

The article is thus divided into three portions (front portion, crotch portion and back portion) in its longitudinal direction, as shown in FIG. 2. The front portion is defined by the waist edge of the article, the longitudinal side edges of the article, part of the leg openings of the article and a transverse line which is located at the point at which the angle of the edge of the leg opening changes most abruptly (i.e. the point at which the rate of change of the angle of the edge of the leg opening with respect to the transverse direction is highest). The back portion is defined in a similar manner: by the waist edge of the article, the longitudinal side edges of the article, part of the leg openings of the article and a transverse line which is located at the point on the edge of the leg opening at which the angle of the edge changes most abruptly (i.e. the point at which the rate of change of the angle of the edge of the leg opening with respect to the transverse direction is highest). The crotch portion is defined on the longitudinal edges by the edges of the leg openings of the article and on the transverse edges by the two transverse lines described above.

It is important that the elastic web material of the front/rear portions is allowed to flex and stretch when the article is in use. If non-elastic layers are joined to this elastic web material, its flexibility and extensibility is reduced. According to embodiments of the invention, the absorbent assembly 3 overlaps no more than 20%, preferably no more than 10%, of the surface area of each of the front and back portions, as measured in an extended state of the article.

The "extended state" of the article is herein defined as a state in which the article has been extended in all four directions to such an extent that all the elastic materials contained therein, such as the elastic web material, the waist elastics, the leg elastics, are extended to such an extent that they will not gather any part of the product, but the entire products is completely flat. The article is extended only to such an extent that this flat condition is reached.

In another embodiment of the invention, the article has a front half 14 defined by the edges of the article and a transverse centre line 16 of the article, and a rear half 15 defined by the edges of the article and a transverse centre line 16 of the article. The surface area of the front half 14 is between 80% and 90% of the surface area of the rear half 15, as measured in an extended state of the article. This provides a more pant-like shape of the absorbent article.

In a further embodiment, the article has a maximum width (c) in the transverse direction and a maximum length (b) in the longitudinal direction, and the ratio of the maximum width (c) to the maximum length (b) of the article is between 80% and 120%, preferably between 90% and 110% as measured in an extended state of the article. According to a preferred embodiment, the ratio of the length (b1) of the front portion to the width (c) of the article (b1/c) is between 25% and 35%, preferably between 28% and 32%, as measured in an extended state of the article. Additionally, the ratio of the length (b3) of the back portion to the width (c) of the article (b3/c) is between 38% and 52%, as measured in an extended state of the article. Articles conforming to these measurements provide a more pant-like shape of the absorbent article and a more secure fit.

To provide good fit and security against leakage, the length (b2) of the crotch portion 7 should be between 10-40%, preferably between 20-40%, most preferably between 25-35% of the entire length of the article (b) as measured in an extended state of the article.

The crotch portion 7 may comprise crotch panel material 21 which underlies the absorbent assembly on the garment-facing side thereof. According to one embodiment of the invention, the crotch panel material 21 comprises substantially inelastic web material 18, although elastic materials may also be used. Suitably, the inelastic web material 18 is a nonwoven material. The substantially inelastic web material 18 is arranged in the crotch portion of the article and may be joined to the elastic web material 10 at or close to the borderline between the crotch portion 7 and the front and back portions 5 and 6 respectively such that it is located between these portions in a longitudinal direction of the article.

Although it may overlap with the front and back portions 5, 6 sufficiently to be joined to these portions, the inelastic web material 18 does not significantly overlap with front or back portions 5,6 over the majority of its surface.

In one embodiment of the invention both of the front and back portions comprise the elastic web material 10, while the crotch portion 7 is substantially free from the elastic web material, wherein the length (b2) of the crotch portion 7 is substantially equal to the distance between panels of the elastic web material 10 in the front and back portions 5 and 6. However the borderline between the front and back portions 5 and 6 and the crotch portion 7 may or may not coincide with the joints between the different panel materials 10 and 21. Thus joints between different panel materials may extend over any of the front, back or crotch portions.

The inelastic web material 18 of the crotch portion 7 may be joined to the elastic web material 10 of the front and/or back portions 5,6 while this is held in a selectively stretched condition, so that gathers are present in the inelastic web material 18 in the front and back crotch portion seams 8,9. The gathers act to draw the pant-type absorbent article to the required shape, thus providing a good fit, and also providing the article with an appearance which is more pant-like.

In another embodiment, no separate crotch panel material 21 is provided, but the elastic web material 10 also underlies the absorbent assembly 3 in the crotch portion of the article. Alternatively, the absorbent assembly 3 alone bridges the front and back portions 5 and 6.

The absorbent assembly 3 according to an embodiment of the invention comprises a liquid impervious backsheet layer 19, a liquid pervious topsheet layer 20 and an absorbent core 2 enclosed therebetween, all of which components are described above. The absorbent assembly 3 may be joined to the elastic web material 10 of the front and/or back portions 5, 6 while this is held in a selectively stretched condition, so that gathers are present in the absorbent assembly 3 at those points where it is joined to the front and back portions 5, 6.

The pant-type absorbent article according to an embodiment of the invention may comprise an elastic waist band 17 comprising elastic members secured to the front and back portion. In an alternative embodiment only one of the front 5 and back portions 6 have an elastic waist band 17 secured thereto. The elastic waist band portions 17 which are secured to the front portion 5 and the back portion 6, respectively, may also be joined to each other along said side seams.

No additional elasticized side portions joining the front and back portions 5 and 6 are needed when using the elastic web material 10. If desired, additional elasticized side portions may of course be provided, especially in cases where the elastic web material 10 is arranged only in parts of the front and/or back portions.

As stated above the elastic web material 10 has an opacity of at least 40%, preferably at least 50% and more preferably at least 60%. The opacity of the elastic web material provides a cloth-like appearance to the article, which is of particular importance when the article is a pant diaper. Especially in this case, where the elastic web material forms the sole component in considerable surface area regions of the pant diaper, such as large areas of the front and back portions, and the absorbent core covers only relatively small areas, 30% or less, of the article, the appearance of the elastic web material is of great importance for the overall appearance of the article. Thus by making the elastic web material opaque with an opacity of at least 40%, the pant diaper will appear more cloth-like and more like "normal" underwear, than if the elastic web material would have a higher degree of transparency. The opacity is measured by the Opacity Test disclosed in PCT/SE2004/001415.

It is further desired that the elastic web material has a puncture resistance of at least 15N as measured according to ASTM Designation D3763-02. Preferably, the elastic web material of the present invention has a puncture resistance of at least 20N, and more preferably at least 30N.

The elastic web material should preferably have a softness according to Kawabata of at least 20, preferably at least 30 and most preferably at least 40. It is further desired that it has a formability according to Kawabata of no more than 50, preferably no more than 30, more preferably no more than 20 and most preferably no more than 10. It is also desired that the elastic web material has a drapability according to Kawabata of no more than 40. The softness, formability and drapability according to kawabata are measured according to the test methods given in PCT/SE2004/001004.

Elasticity Test

The method measures how an elastic material behaves at repeated load and unload cycles. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotteror software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

| | |
|---|---|
| Crosshead speed: | 500 mm/min |
| Clamp distance: | 50 mm |
| Preload: | 0.05 N |

The sample is placed in the clamps according to the marks and it is made sure that the sample is centred and fastened perpendicularly in the clamps. The tensile tester is started and three cycles between 0 and the predetermined elongation, equal to the highest defined 1st load, are performed. Before the last cycle, the sample is relaxed for 1 minute, and the permanent elongation is measured by stretching the sample until a force of 0.1 N is detected and the elongation is read.

The permanent elongation after relaxation should be less than 10% and is measured by the method above. Thus an elasticity of 30% is defined as that the laminate should have a permanent relaxation after elongation of less than 10% after being exerted to an elongation of 30% in the tensile tester above. An elongation of 30% means an elongation to a length that is 30% longer than the initial length of the sample.

Dimensions

Some embodiments of the inventive articles have the following dimensions and relative dimensions:

| Product | Product width (c)/ product length (b); % | Back portion length (b3)/ product width (c); % | Front portion length (b1)/ product width (c); % | Crotch portion length (b2)/ product width (c); % | Crotch portion length (b2)/ product length (b); % |
|---|---|---|---|---|---|
| 1 | 92 | 47 | 29 | 24 | 26 |
| 2 | 92 | 50 | 32 | 18 | 20 |
| 3 | 108 | 39 | 30 | 31 | 29 |

Overlap of Absorbent Assembly on Front/Back Portions

| Product | % Overlap, back | % Overlap, back |
|---|---|---|
| 1 | 15 | 5 |
| 2 | 12 | 12 |

It is understood that although the invention has been described with reference to preferred embodiments, several modifications are possible within the scope of the claims and equivalents thereof. The invention therefore intends to cover any variations or equivalents which are within known or customary practice within the technical field to which it belongs.

What is claimed is:

1. A pant-type absorbent article comprising an absorbent assembly comprising an absorbent core and a chassis, said chassis comprising a front portion and a back portion, wherein the front and back portions are joined to each other along two opposite longitudinal side edges to define a waist-opening and a pair of leg-openings, at least one of the front and back portions comprises an elastic web material, said article further comprising a crotch portion located between the front portion and the back portion in the longitudinal direction of the article, said front portion having a length (b1) in the longitudinal direction, said back portion (6) having a length (b3) in the longitudinal direction, and said crotch portion having a length (b2) in the longitudinal direction, said absorbent assembly lying at least in said crotch portion and overlapping a certain distance with both the front and back portions, said article having a front half defined by the edges of the article and a transverse centre line of the article, and a rear half defined by the edges of the article and a transverse centre line of the article, said article having a longitudinal (y) and a transverse direction (x), wherein a surface area of the front half is between 80% and 90% of a surface area of the rear half, as measured in an extended state of the article.

2. A pant-type absorbent article comprising an absorbent assembly comprising an absorbent core and a chassis, said chassis comprising a front portion and a back portion, wherein the front and back portions are joined to each other along two opposite longitudinal side edges to define a waist-opening and a pair of leg-openings, at least one of the front and back portions comprises an elastic web material, said article further comprising a crotch portion located between the front portion and the back portion in the longitudinal direction of the article, said front portion having a length (b1) in the longitudinal direction, said back portion having a length (b3) in the longitudinal direction, and said crotch portion having a length (b2) in the longitudinal direction, said absorbent assembly lying at least in said crotch portion and overlapping a certain distance with both the front and back portions, said article having a maximum width (c) in the transverse direction and a maximum length (b) in the longitudinal direction, said article having a longitudinal (y) and a transverse direction (x) wherein:
- a ratio of the maximum width (c) to the maximum length (b) of the article is between 80% and 120 as measured in an extended state of the article;
- a ratio of the length of the front portion (b1) to the maximum width (c) of the article is between 25% and 35 as measured in an extended state of the article; and
- a ratio of the length of the back portion (b3) to the maximum width (c) of the article is between 38% and 52%, as measured in an extended state of the article.

3. The pant-type absorbent article according to claim 2, wherein
a ratio of the length of the front portion (b1) to the maximum width (c) of the article is between 28% and 32% as measured in an extended state of the article.

4. The pant-type absorbent article according to claim 1, wherein
the length (b2) of the crotch portion is between 10-40% of the entire length of the article (b) as measured in an extended state of the article.

5. The pant-type absorbent article according to claim 2, wherein
the length (b2) of the crotch portion is between 10-40% of the entire length of the article (b) as measured in an extended state of the article.

6. The pant-type absorbent article according to claim 1, wherein
the length (b2) of the crotch portion is between 25-35% of the entire length of the article (b) as measured in an extended state of the article.

7. The pant-type absorbent article according to claim 2, wherein
the length (b2) of the crotch portion is between 25-35% of the entire length of the article (b) as measured in an extended state of the article.

8. The pant-type absorbent article according to claim 1, wherein, both of the front and back portions comprise said elastic web material.

9. The pant-type absorbent article according to claim 2, wherein, both of the front and back portions comprise said elastic web material.

10. The pant-type absorbent article according to claim 1, wherein the absorbent assembly comprises a liquid impervious backsheet layer, a liquid pervious topsheet layer and an absorbent core enclosed therebetween.

11. The pant-type absorbent article according to claim 2, wherein the absorbent assembly comprises a liquid impervious backsheet layer, a liquid pervious topsheet layer and an absorbent core enclosed therebetween.

12. The pant-type absorbent article according to claim 1, wherein the crotch portion comprises a crotch panel material underlying the absorbent assembly on the garment facing side thereof.

13. The pant-type absorbent article according to claim 2, wherein the crotch portion comprises a crotch panel material underlying the absorbent assembly on the garment facing side thereof.

14. The pant-type absorbent article according to claim 12, wherein
the crotch panel material comprises substantially inelastic web material.

15. The pant-type absorbent article according to claim 13, wherein
the crotch panel material comprises substantially inelastic web material.

16. The pant-type absorbent article according to claim 14, wherein the inelastic web material is a nonwoven material.

17. The pant-type absorbent article according to claim 15, wherein the inelastic web material is a nonwoven material.

18. The pant-type absorbent article according to claim 1, wherein the elastic web material is a laminate composed of first and second layers of fibrous material and an elastic film layer located between said first and second fibrous layers.

19. The pant-type absorbent article according to claim 2, wherein the elastic web material is a laminate composed of first and second layers of fibrous material and an elastic film layer located between said first and second fibrous layers.

20. The pant-type absorbent article according to claim 18, wherein
said elastic film layer is breathable.

21. The pant-type absorbent article according to claim 19, wherein
said elastic film layer is breathable.

22. The pant-type absorbent article according to claim 20, wherein
said elastic laminate has a Water Vapour Transmission Rate according to ASTM E96-00 Procedure D of at least 1500 g/m2 24 h.

23. The pant-type absorbent article according to claim 21, wherein
said elastic laminate has a Water Vapour Transmission Rate according to ASTM E96-00 Procedure D of at least 1500 g/m2 24 h.

24. The pant-type absorbent article as claimed in claim 18, wherein said laminate comprises first and second fibrous layers of spunbond material, each having a basis weight of between 10 and 35 g/m2 and a breathable elastic film layer having a basis weight between 20 and 80 g/m2 said elastic laminate having a Water Vapour Transmission Rate according to ASTM E96-00 Procedure D of at least 1500 g/m2 24 h.

25. The pant-type absorbent article as claimed in claim 19, wherein said laminate comprises first and second fibrous layers of spunbond material, each having a basis weight of between 10 and 35 g/m2 and a breathable elastic film layer having a basis weight between 20 and 80 g/m2 said elastic laminate having a Water Vapour Transmission Rate according to ASTM E96-00 Procedure D of at least 1500 g/m2 24 h.

26. The pant-type absorbent article according to claim 1, wherein the elastic web material has a basis weight of no more than 100 g/m2.

27. The pant-type absorbent article according to claim 2, wherein the elastic web material has a basis weight of no more than 100 g/m2.

28. The pant-type absorbent article according to claim 1, wherein said elastic web material has an elasticity in the transverse direction of the article of at least 30% when measured according to the elasticity test specified in the description.

29. The pant-type absorbent article according to claim 2, wherein said elastic web material has an elasticity in the transverse direction of the article of at least 30% when measured according to the elasticity test specified in the description.

30. The pant-type absorbent article according to claim 1, wherein the elastic web material has an elasticity in the longitudinal direction of the article of at least 20% when measured according to the elasticity test specified in the description.

31. The pant-type absorbent article according to claim 2, wherein the elastic web material has an elasticity in the longitudinal direction of the article of at least 20% when measured according to the elasticity test specified in the description.

32. A pant-type absorbent article, said article comprising an absorbent assembly comprising an absorbent core and a chassis, said chassis comprising a front portion and a back portion, wherein the front and back portions are joined to each other along two opposite longitudinal side edges to define a waist-opening and a pair of leg-openings, at least one of the front and back portions comprises an elastic web material, said article further comprising a crotch portion located between the front portion and the back portion in the longitudinal direction of the article, said front portion having a length in the longitudinal direction, said back portion having a length in the longitudinal direction, and said crotch portion having a length in the longitudinal direction, said absorbent assembly lying at least in said crotch portion and overlapping a certain distance with both the front and back portions, said article having a longitudinal (y) and a transverse direction (x), wherein
a ratio of the length (b1) of the front portion of the article to the maximum width (c) of the article is between 25% and 35%, as measured in an extended state of the article; and
a ratio of the length (b3) of the back portion of the article to the maximum width (c) of the article is between 38% and 52%.

33. The pant-type article according to claim 32, wherein a ratio of the maximum width (c) to the maximum length (b) of the article is between 80% to 120%, as measured in an extended state of the article.

* * * * *